United States Patent
Biber

(10) Patent No.: US 10,429,481 B2
(45) Date of Patent: Oct. 1, 2019

(54) CALIBRATING A MAGNETIC RESONANCE APPARATUS

(71) Applicant: Stephan Biber, Erlangen (DE)

(72) Inventor: Stephan Biber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/850,736

(22) Filed: Dec. 21, 2017

(65) Prior Publication Data

US 2018/0172792 A1 Jun. 21, 2018

(30) Foreign Application Priority Data

Dec. 21, 2016 (DE) .................. 10 2016 225 793

(51) Int. Cl.
G01R 33/58 (2006.01)
A61B 5/055 (2006.01)
G01R 33/34 (2006.01)
G01R 33/36 (2006.01)

(52) U.S. Cl.
CPC .......... *G01R 33/583* (2013.01); *A61B 5/055* (2013.01); *G01R 33/34046* (2013.01); *G01R 33/3614* (2013.01); *G01R 33/58* (2013.01); *A61B 2560/0223* (2013.01)

(58) Field of Classification Search
CPC .. G01R 33/58; G01R 33/583; G01R 33/3614; G01R 33/34046; A61B 5/055
See application file for complete search history.

(56) References Cited

U.S. PATENT DOCUMENTS

| 3,879,653 | A | * | 4/1975 | Hyde | ...................... | G01R 33/60 |
| | | | | | | 324/316 |
| 6,564,081 | B1 | * | 5/2003 | Frigo | ................... | G01R 33/3621 |
| | | | | | | 324/307 |
| 6,842,003 | B2 | | 1/2005 | Heid et al. | | |
| 7,518,367 | B2 | | 4/2009 | Renz et al. | | |
| 7,800,368 | B2 | * | 9/2010 | Vaughan | ............... | G01R 33/583 |
| | | | | | | 324/318 |
| 8,013,605 | B2 | | 9/2011 | Matschl | | |

(Continued)

FOREIGN PATENT DOCUMENTS

DE 102013206570 B3 5/2014
DE 102013214867 A1 2/2015

OTHER PUBLICATIONS

German Office Action for German Application No. 102016225793.5, dated Oct. 6, 2017.

*Primary Examiner* — Dixomara Vargas
(74) *Attorney, Agent, or Firm* — Lempia Summerfield Katz LLC

(57) ABSTRACT

A method for calibrating at least one operating parameter of a magnetic resonance apparatus and a corresponding magnetic resonance apparatus and computer program product are provided. The at least one operating parameter includes a constant component and a variable component. The method includes, after a start-up of at least one part of the magnetic resonance apparatus, determining the variable component of the at least one operating parameter. The constant component of the at least one operating parameter is provided. The constant component and the variable component are used to calibrate the at least one operating parameter.

15 Claims, 4 Drawing Sheets

(56) References Cited

U.S. PATENT DOCUMENTS

| | | | | |
|---|---|---|---|---|
| 8,244,192 B2* | 8/2012 | Prasidh | ............. | G01R 33/3692 |
| | | | | 324/307 |
| 9,581,669 B2* | 2/2017 | Bollenbeck | ............ | G01R 33/56 |
| 10,067,211 B2* | 9/2018 | Dagher | ............. | G01R 33/5608 |
| 2014/0307764 A1 | 10/2014 | Adolf et al. | | |
| 2015/0035531 A1 | 2/2015 | Stemmer | | |

* cited by examiner

CALIBRATING A MAGNETIC RESONANCE APPARATUS

This application claims the benefit of German Patent Application No. DE 10 2016 225 793.5, filed on Dec. 21, 2016, which is hereby incorporated by reference in its entirety.

BACKGROUND

The present embodiments relate to calibrating at least one operating parameter of a magnetic resonance apparatus.

Magnetic resonance imaging (MRI) is a known technique for generating images of the interior of a patient's body based on the physical phenomenon of magnetic resonance (MR).

A magnetic resonance apparatus may include a permanently installed body coil (BC) that may be operated as a transmit and receive coil. Body coils are, for example, described in publications U.S. Pat. Nos. 6,842,003 B2, 7,518,367 B2, and 8,013,605 B2. As a transmit coil, a body coil emits radio-frequency excitation signals, thus causing the excitation of atomic nuclei in the patient's body. The excited atomic nuclei emits magnetic resonance signals that may be received by the body coil or even a local coil as a receive coil. A receive coil may include a plurality (e.g., 2, 4, 8, 16, 32, 64, etc.) of antennas that together form an antenna array. The antennas are each able to receive magnetic resonance signals independently of one another and forward the magnetic resonance signals on a respective receive channel for further processing.

The first tune-up of a magnetic resonance apparatus is generally also accompanied by calibration of the magnetic resonance apparatus. For example, a service technician uses a phantom to determine a phase relationship between the plurality of independent receive channels of the body coil. This enables the use of image-combination methods based on a phase-weighted combination, a "BC combine", of individual images. The image-combination methods help to improve image quality (e.g., homogeneity).

SUMMARY AND DESCRIPTION

The scope of the present invention is defined solely by the appended claims and is not affected to any degree by the statements within this summary.

The present embodiments may obviate one or more of the drawbacks or limitations in the related art. For example, the calibration of at least one operating parameter of a magnetic resonance apparatus such as a body coil is simplified.

A method for calibrating at least one operating parameter of a magnetic resonance apparatus (e.g., a body coil) is provided. The at least one operating parameter includes a constant component and a variable component. The method includes determining the variable component of the at least one operating parameter following a start-up of at least one part of the magnetic resonance apparatus. In addition, the constant component of the at least one operating parameter is provided. The constant component and the variable component are used to calibrate the at least one operating parameter.

On start-up, it is not necessary to start all the components of the magnetic resonance apparatus. The at least one part of the magnetic resonance apparatus that is started may include parts of which the start-up leads to a change in the at least one operating parameter (e.g., to a change in the variable component of the operating parameter). This may, for example, be a component that generates and/or processes a clock signal. Therefore, hereinafter, a start-up of a magnetic resonance apparatus may also be understood to be that only one part of the magnetic resonance apparatus may be affected thereby.

A clock signal (e.g., a system clock or clock) may be a signal for coordinating and/or synchronizing actions of a plurality of circuits within digital and/or analog systems. Depending upon the application, the clock signal may be repeated with a defined frequency (e.g., the clock frequency) or even periodically.

Herein, the at least one operating parameter (e.g., the variable component of the operating parameter) may change with respect to a previous operation of the magnetic resonance apparatus before the start or restart of the magnetic resonance apparatus. In other words, the at least one operating parameter (e.g., the variable component of the operating parameter) changes due to the magnetic resonance apparatus being switched off and on.

Subdivision into a constant and a variable component of the at least one operating parameter enables the determination of the constant component after the start-up of the magnetic resonance apparatus to be dispensed with and hence simplifies the calibration. Only the variable component is to be determined, for example.

The constant component may be determined once in advance (e.g., on the tune-up of the magnetic resonance apparatus) during, for example, the tune-up and/or installation and/or commissioning of the magnetic resonance apparatus. The at least operating parameter as a whole (e.g., a combination of the constant and the variable component) and the variable component may be determined. The constant component may then be derived from the combination of the constant component and the variable component determined and from the variable component determined.

The constant component of the at least one operating parameter is provided from a persistent memory in which the constant component is stored following determination. The persistent memory retains information following on an interruption to a power supply.

The magnetic resonance apparatus may include a first measuring unit configured to determine the variable component.

The first measuring unit may, for example, include a clock generator and/or a test signal generator and/or a signal acquisition unit (e.g., an analog and/or receiving unit). The clock generator triggers the test signal generator and the signal acquisition unit (e.g., the clock generator transmits a trigger signal to the test signal generator and to the signal acquisition unit). The test signal generator generates a test signal triggered by the clock generator, which is coupled into a signal path of a section of the magnetic resonance apparatus that determines the variable component of the at least one operating parameter. In one embodiment, therefore, the section includes a transmission link through which the test signal passes. The test signal transmitted over the signal path of the section may be compared with the trigger signal that was transmitted directly from the clock generator to the signal acquisition unit in order to determine the variable component of the at least one operating parameter (e.g., a signal phase). Herein, the signal acquisition unit may, for example, be configured as a digital acquisition unit. The comparison of the trigger signal and the test signal may, for example, be performed by a measurement acquisition and reconstruction system (MARS). The measurement acquisition and reconstruction system may include a computer with control hardware.

The constant component and/or the combination of the constant component and the variable component may be determined with a further measuring unit of the magnetic resonance apparatus and/or with an external measuring unit. The external measuring unit may, for example, be used by a service technician when tuning-up the magnetic resonance apparatus (e.g., temporarily only).

The further measuring unit may, for example, include at least one part of the first measuring unit. For example, a magnetic resonance signal, which is, for example, generated in a phantom and/or a patient, may be coupled-in via a signal path of a extended section of the magnetic resonance apparatus that determines the variable component and the constant component (e.g., a combination of the constant component and the variable component) of the at least one operating parameter. In one embodiment, therefore, the extended section includes a transmission link through which the magnetic resonance signal passes. The magnetic resonance signal transmitted via the signal path of the extended section may be acquired by the signal acquisition unit and evaluated by the measurement acquisition and reconstruction system. The constant component of the at least one operating parameter may be determined from the variable component and the combination of the constant and the variable component.

In one embodiment, the first measuring unit and/or further measuring unit and/or external measuring unit may include a measuring device (e.g., one or more network analyzers configured to carry out transmission and/or reflection measurements with respect to amount and phase). In one embodiment, any lines and/or switches may be suitably connected. The magnetic resonance apparatus may further include a calibrating unit with which the at least one operating parameter may be calibrated using the constant component and the variable component. The calibrating unit may, for example, be included by the measurement acquisition and reconstruction system.

The start-up may include a boot-up (e.g., reboot) of at least one part of the magnetic resonance apparatus and/or a switching-on (e.g., re-switching-on) of at least one part of the magnetic resonance apparatus and/or a restoration of a power supply (e.g., after a power outage of at least one part of the magnetic resonance apparatus). For example, this at least one part of the magnetic resonance apparatus includes one or more components that, following a start (e.g., restart) of the magnetic resonance apparatus cause a change to the variable component of the at least one operating parameter. The determination of the variable component may enable this change to be compensated once again.

The start-up of the magnetic resonance apparatus, caused, for example, by a power outage, may be identified by the magnetic resonance apparatus, whereupon the determination of the variable component, the provision of the constant component, and the calibration of the at least one operating parameter based thereupon, takes place, possibly for a repeat time.

Therefore, the magnetic resonance apparatus may be recalibrated as soon as the magnetic resonance apparatus has been restarted. An identification (e.g., automatic identification) of the start-up enables it to be provided that the at least one operating parameter is always correctly calibrated.

One embodiment of the method provides that the at least one operating parameter includes a signal phase between at least two signal channels of the magnetic resonance apparatus. For example, the at least one operating parameter consists of at least one signal phase. Herein, a signal phase may be understood to be a phase relationship and/or phase angle and/or phase relation and/or phase shift and/or phase difference and/or phase angle between two or more signals that are each routed on a signal channel.

This aspect is based on the finding that calibrating the signal phase may be broken down into two components. Herein, the phase relation of one component remains constant between two start-ups, while a further component remains constant in this regard. This division and the possibility of being able to recalibrate the latter component automatically after a start-up without operator intervention enables the resolution of any phase relation problems.

In one embodiment, the at least two signal channels include transmit channels (e.g., for the generation of magnetic resonance signals) and/or receive channels (e.g., for the reception of magnetic resonance signals). A signal channel may, for example, be understood to be a transmission path of an electrical signal.

Phase calibration of the body-coil receive chain may be carried out to provide phase rigidity, even after a system reboot.

A transmit channel may be a signal channel on which transmit signals are routed electrically to a transmit coil (e.g., a transmit antenna of the transmit coil) on a transmit path. The transmit antenna may use the transmit signals to generate electromagnetic excitation signals, which, as described above, may be used to excite atomic nuclei and hence to generate magnetic resonance signals.

A receive channel may be a signal channel that routes magnetic resonance signals received from a receive coil (e.g., from a receive antenna of the receive coil) electrically on a receive path.

In one embodiment, the transmit path and the receive path may include the same components. For example, a receive antenna may also be used as a transmit antenna (e.g., by switching from a receive mode into a transmit mode and vice versa).

Correct calibration of the signal phase between two or more receive channels is, for example, important in the case of complex image-combination methods based on a phase-weighted combination.

One embodiment of the method provides that the at least two signal channels each include a signal path with a first section and a second section. The constant component of the at least one operating parameter is determined by the first section, and the variable component of the at least one operating parameter is determined by the second section.

A further embodiment of the method provides that the at least two signal channels each include a signal path with a first section and a second section. The constant component of the at least one operating parameter is determined using the first section, and the variable component of the at least one operating parameter is determined using the second section.

In one embodiment, a signal path of a signal channel may be divided into at least two sections. In one embodiment, the second section then includes one or more components that cause a change to the variable component of the at least one operating parameter after a start-up of the magnetic resonance apparatus. The determination of the variable component enables this change to be compensated again. The first section may include one or more components that do not cause any change to the variable component of the at least one operating parameter.

Dividing the signal paths into at least two sections enables the constant component and/or the variable component of the at least one operating parameter to be specifically determined.

In one embodiment, the second section includes at least one component that generates and/or processes a clock signal. For example, the second section does not include a component that generates and/or processes a clock signal.

Typically, components that generate or process a clock signal aggravate phase relation problems so that, on a re-start, in conventional systems, phase rigidity of the signal channels is no longer provided. For example, such components are typically de-energized on boot-down so that following a reboot, the phase relationships of the signal channels no longer match those before the boot-down. Calibration of the at least one operating parameter (e.g., of the signal phase) enables this to be corrected once again.

For example, between two boot-ups of the magnetic resonance apparatus, a change in the phases of a clock generator that generates the clock signal may cause the signal phase to change at different assemblies of a receive chain so that, for example, the signal phase no longer matches the signal phase that may have been determined on the commissioning of the magnetic resonance apparatus. The proposed method enables cumbersome repeated calibration of the entire receive chain by a specially trained service technician, which typically requires the repositioning of a phantom, to be dispensed with.

In one embodiment, the first section includes one transmission link of an excited atomic core to a receive antenna and/or a transmission link from the receive antenna to a body-coil channel selector (BCCS) (e.g., to a switching matrix of the body-coil channel selector). The first section may further include a transmission link from a transmit antenna to an atomic nucleus to be excited and/or a transmission link from a body-coil channel selector (e.g., from a switching matrix of the body-coil channel selector) to the transmit antenna.

The body-coil channel selector may be configured to switch the magnetic resonance apparatus between a transmit mode in a receive mode and vice versa. The body-coil channel selector may, for example, in transmit mode, connect the body coil to a radio-frequency power amplifier (RFPA). The body-coil channel selector may, for example, include one or more switching matrices and/or one or more amplifiers (e.g., low-noise converters (LNC) and/or one or more directional couplers).

The second section may include a transmission link from the body-coil channel selector (e.g., from the switching matrix of the body-coil channel selector) to a receive-coil channel selector (RCCS) and/or a transmission link from the receive-coil channel selector to an analog receiving unit and/or a transmission link from the analog receiving unit to a digital receiving unit (e.g., to an output of the digital receiving unit connecting the digital receiving unit to a measurement acquisition and reconstruction system).

The receive-coil channel selector may be configured to switch one or more receive coils to one or more receivers. The analog receiving unit is, for example, configured to digitize and/or process a signal (e.g., to equalize a frequency response). The digital receiving unit is, for example, configured to change (e.g., reduce) a data rate.

A further embodiment of the method provides that for the determination of the variable component of the at least one operating parameter, a test signal is applied simultaneously and/or in series to the at least two transmit channels. The test signal may be used to determine the phase relations.

This is particularly advantageous when the magnetic resonance apparatus includes more than two signal channels. Herein, the test signal, which is, for example, generated by a test signal generator, is sent simultaneously and/or in series via a signal distributor to a plurality of signal channels (e.g., receive channels) that are then calibrated with respect to one another.

Also provided is a magnetic resonance apparatus configured to carry out an above-described method for calibrating at least one operating parameter of the magnetic resonance apparatus.

The advantages of the magnetic resonance apparatus according to the present embodiments substantially correspond to the advantages of the method according to the present embodiments for calibrating at least one operating parameter of a magnetic resonance apparatus, which are described in detail above. Features, advantages or alternative embodiments mentioned herein may also be transferred to the magnetic resonance apparatus and vice versa.

In other words, the embodiments of the apparatus may also be developed with the features that are described in connection with a method. Herein, the corresponding functional features of the method are embodied by corresponding material modules (e.g., by hardware modules).

For example, a magnetic resonance apparatus that includes at least one clock generator is provided.

In one embodiment, the magnetic resonance apparatus includes a measuring unit that is embodied to determine a variable component of at least one operating parameter and/or a one calibrating unit that is embodied to use a constant component and a variable component of at least one operating parameter to calibrate the at least one operating parameter.

In one embodiment, a computer program product that includes a program and may be loaded directly into a memory of a programmable computing unit of a calibrating unit of a magnetic resonance apparatus, and programs (e.g., libraries and auxiliary functions) for carrying out a method for calibrating at least one operating parameter of a magnetic resonance apparatus when the computer program product is executed in the calibrating unit are provided. The computer-program product may include software with a source code that still is to be compiled and linked or only is to be interpreted, or an executable software code that only is to be loaded into the calibrating unit for execution. The computer-program product may carry out the method, repeatably and robustly. The computer-program product is configured such that the computer-program product may use the calibrating unit to carry out the method acts according to the present embodiments. Herein, the calibrating unit advantageously includes the prerequisites, such as, for example, a corresponding main memory or a corresponding logic unit, thus enabling the respective method acts to be carried out efficiently.

BRIEF DESCRIPTION OF THE DRAWINGS

In all figures, corresponding parts are given the same reference numbers.

DETAILED DESCRIPTION

Figure 1:
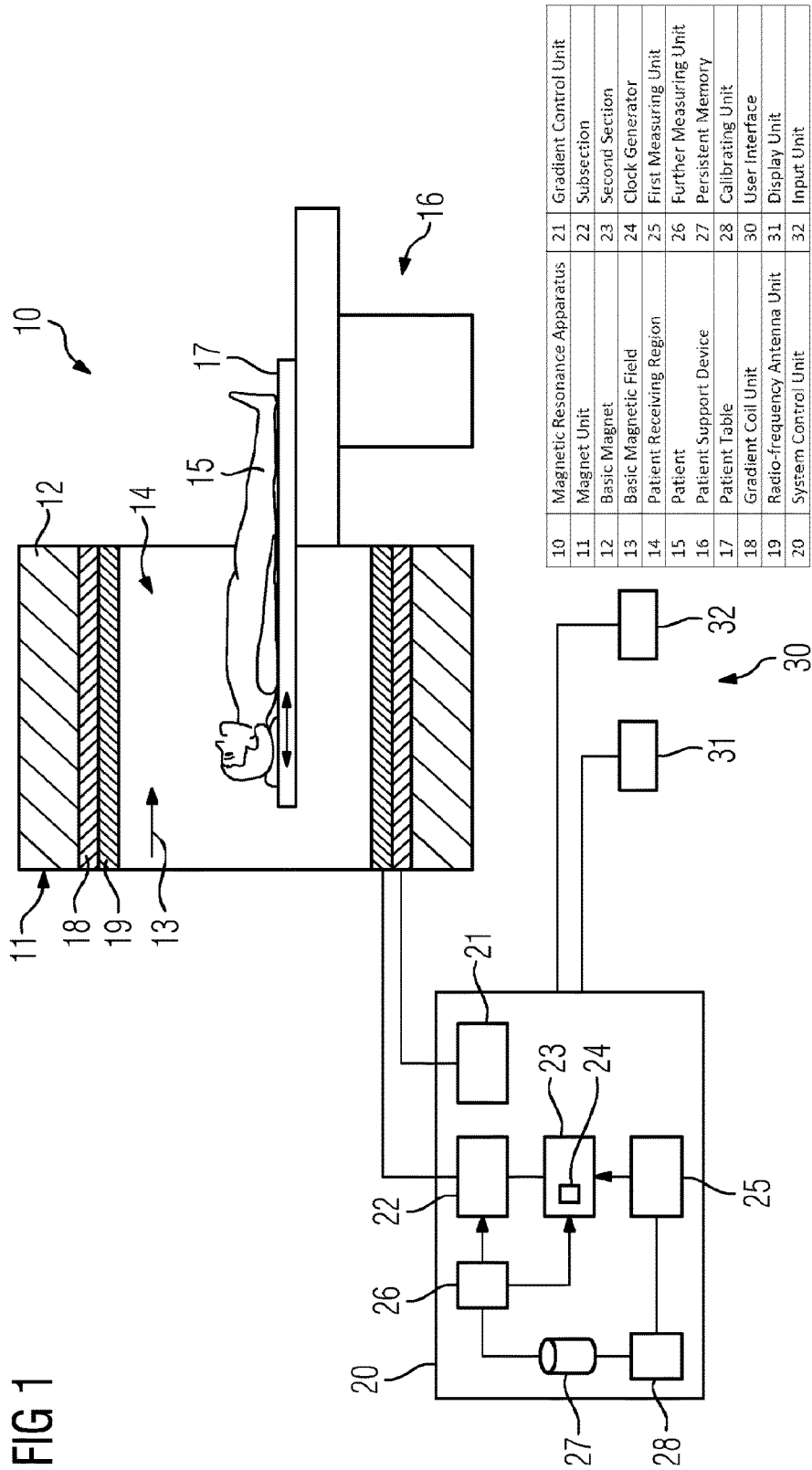
FIG. 1 shows one embodiment of a magnetic resonance in a schematic representation.

FIG. 1 is a schematic representation of one embodiment of a magnetic resonance apparatus 10. The magnetic resonance apparatus 10 includes a magnet unit 11 including a basic magnet 12 for the generation of a strong and, for example, temporally constant basic magnetic field 13. The magnetic resonance apparatus 10 also has a patient receiving region 14 for receiving a patient 15. When calibrating the magnetic resonance apparatus 10, it is also possible for a phantom to be arranged in the patient receiving region 14 instead of the patient.

In the present exemplary embodiment, the patient receiving region 14 is embodied as cylindrical and cylindrically enclosed in a circumferential direction by the magnet unit 11. An embodiment of the patient receiving region 14 different from this may, however, be provided. The patient 15 may be pushed into the patient receiving region 14 by a patient support device 16 of the magnetic resonance apparatus 10. The patient support device 16 includes a patient table 17 arranged in a movable manner within the patient receiving region 14.

The magnet unit 11 further includes a gradient coil unit 18 for generating magnetic field gradients that are used for spatial encoding during imaging. The magnetic resonance apparatus 10 includes a system control unit 20 that controls the magnetic resonance apparatus 10 centrally, such as, for example, the performance of a predefined pulse sequence. The system control unit 20, for example, includes a gradient control unit 21 for controlling the gradient coil unit 18.

The magnet unit 11 further includes a radio-frequency antenna unit 19 that, in the present exemplary embodiment, is configured as a body coil permanently integrated in the magnetic resonance apparatus 10. The radio-frequency antenna unit 19 is tuned to emit radio-frequency excitation signals for the excitation of atomic nuclei, which are established in the basic magnetic field 13 generated by the basic magnet 12 and configured to receive magnetic resonance signals resulting from the excitation. For the correct operation of the magnetic resonance apparatus 10 (e.g., the radio-frequency antenna unit 19), it is possible to set (e.g., calibrate) operating parameters.

The radio-frequency antenna unit 19 may include a plurality of antennas, for example, each with a signal channel on which any signals may be supplied to the antenna and/or routed away from the antenna. Depending upon whether the radio-frequency antenna unit 19 is transmitting or receiving signals, these are transmit or receive channels.

The signal channels each have a signal path. The signal path may be divided into a first section including the radio-frequency antenna unit 19 and a first section 22 and a second section 23. The first section 22 influences a constant component of an operating parameter, and the second section 23 influences a variable component of the operating parameter, such as, for example, a signal phase between two signal channels. The variable component may change after each start-up of the magnetic resonance apparatus while the constant component is not affected thereby.

The second section 23 includes a clock generator 24 that generates a clock signal, and the clock signal, for example, provides further components of the second section to process the clock signal. An interruption to the power supply (e.g., a deliberate boot-down of the magnetic resonance apparatus 10 or an unwanted power outage) may cause the variable component of the operating parameter to change. The system control unit 20 includes a first measuring unit 25 configured to determine the variable component.

The magnetic resonance apparatus 10 optionally includes a further measuring unit 26 with which the constant component of the operating parameter and/or a combination of the constant and variable component of the operating parameter may be determined. In one embodiment, the constant component may be derived from the variable component, and the combination of the constant component and the variable component may be derived.

The first measuring unit 25 and the further measuring unit 26 may also include common components, such as, for example, an evaluating unit that is not shown in FIG. 1, including, for example, one or more processors and a memory. Measuring signals may be transmitted to the evaluating unit from which the operating parameter (e.g., the variable and/or constant component of the operating parameter) is determined.

However, the variable component and the combination of the constant component and the variable component may also be determined by an external measuring unit that, for example, is used by a service technician during the commissioning of the magnetic resonance apparatus 10, but does not remain permanently on the magnetic resonance apparatus 10 (e.g., it is not necessary for that the magnetic resonance apparatus 10 to include the further measuring unit 26).

The system control unit 20 includes a persistent memory 27, in which the constant component may be filed. The system control unit 20 further includes a calibrating unit 28 that may be provided with the constant component from the persistent memory 27 and the variable component by the first measuring unit 25. The calibrating unit 28 is configured to calibrate the operating parameter using the constant component and the variable component. To this end, the calibrating unit 28 may include one or more processors and a memory. The memory may be loaded with a program of a computer-program product with program code in order to carry out a method for calibrating at least one operating parameter of a magnetic resonance apparatus when the program is executed in the calibrating unit of the magnetic resonance apparatus.

In one embodiment, the first measuring unit 25 and/or the further measuring unit 26 and/or the calibrating unit 28 may include common components in that the first measuring unit 25 and/or the further measuring unit 26 and/or the calibrating unit 28, for example, includes one or more common processors and/or a common memory, respectively.

In addition, the system control unit 20 includes a reconstruction unit, which is not depicted in further detail, for the reconstruction of medical image data acquired during the magnetic resonance examination. The magnetic resonance apparatus 10 further includes a user interface 30 connected to the system control unit 20. Control information such as, for example, imaging parameters and reconstructed magnetic-resonance images may be displayed on a display unit 31 (e.g., on at least one monitor) of the user interface 30 for a medical operator. The user interface 30 further includes an input unit 32 by which the information and/or parameters may be input by the medical operator during a measuring process.

Figure 2:
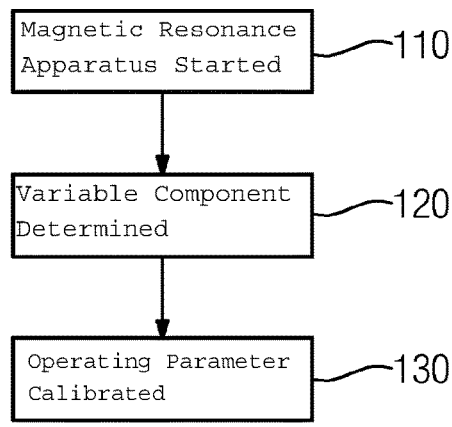
FIG. 2 is a block diagram of one embodiment of a method.

FIG. 2 is a schematic representation of one embodiment of a method for calibrating at least one operating parameter including a constant component and a variable component. In act 110, the magnetic resonance apparatus is started. The start-up may include a boot-up and/or switching-on and/or restoration of a power supply of at least one part of the magnetic resonance apparatus. The start-up of the magnetic resonance apparatus in 110 may be identified by the magnetic resonance apparatus 10, whereupon the following acts 120 and 130 are carried out. To identify the start-up, the magnetic resonance apparatus 10 includes, for example, an identifying unit that is not shown in FIG. 1, which, for example, includes electrical circuits that register a power interruption.

In act 120, the variable component of the operating parameter is determined, for example, by the first measuring unit 25. In act 120, the constant component of the operating parameter is provided, for example, from the persistent memory 27. The constant component may, for example, be determined once in advance (e.g., by a service technician using the further measuring unit 26 or an external measuring unit).

In act 130, the at least one operating parameter is calibrated using the constant component and the variable component. The calibration may include the tune-up of the at least one operating parameter (e.g., the at least one operating parameter is recalibrated).

Figure 3:
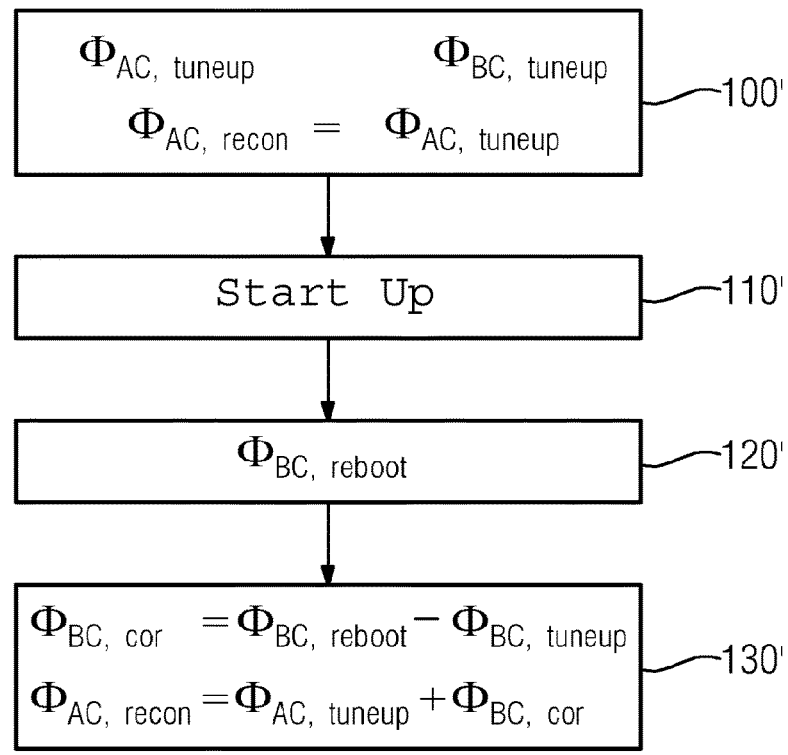
FIG. 3 is a block diagram of one embodiment of a method.
Figure 4:
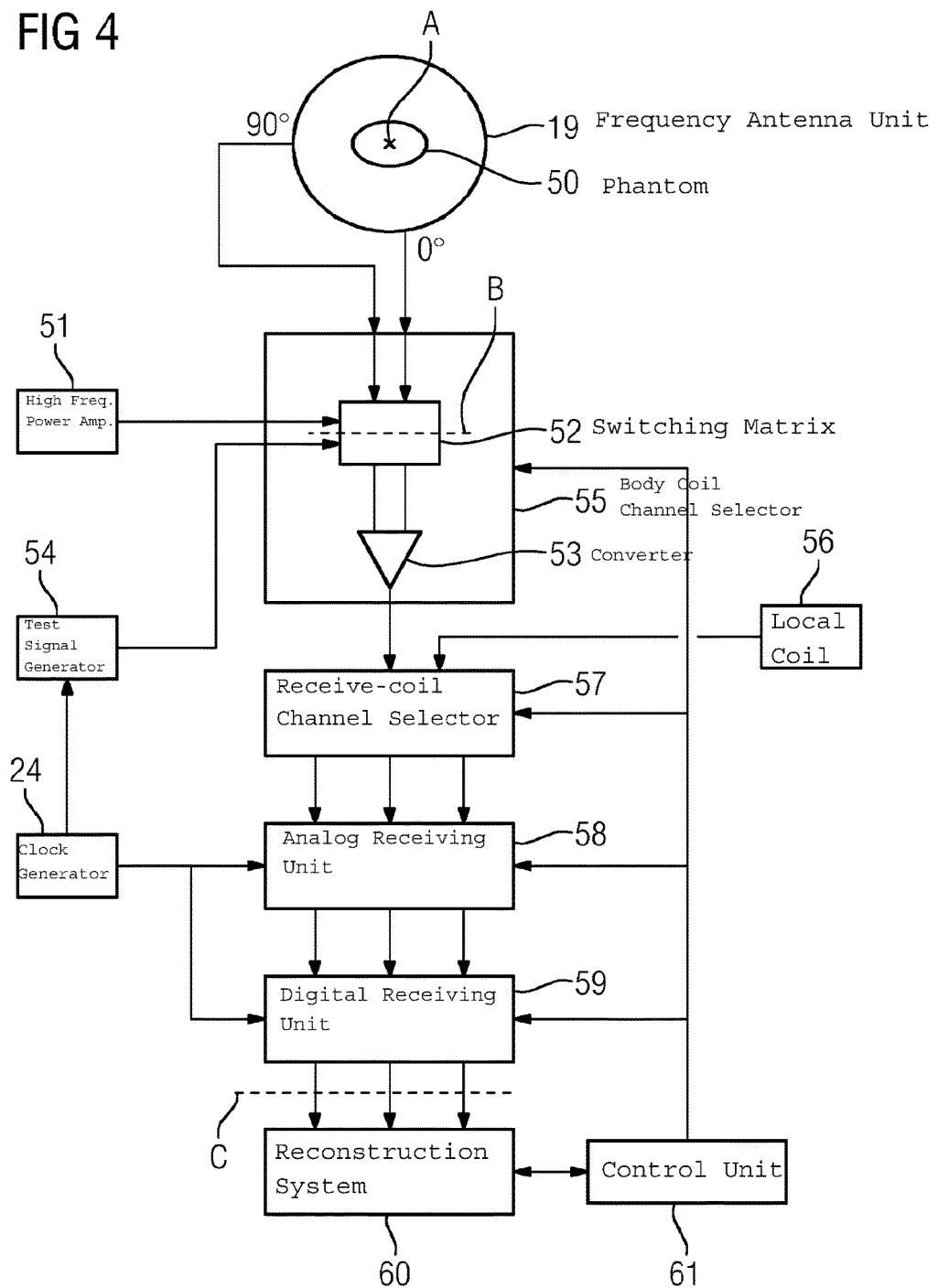
FIG. 4 shows a block diagram of a first variant of a receive path.

FIG. 3 and FIG. 4 illustrate by way of example further embodiments of a method and a magnetic resonance apparatus 10. FIG. 4 is a block diagram of a receive path with two receive channels 0° and 90° of a radio-frequency antenna unit 19, in which a phantom 50 is located on a first tune-up of the magnetic resonance apparatus 10 for the calibration.

The receive path includes a body-coil channel selector 55 with a switching matrix 52 that is connected to a radio-frequency power amplifier 51, and a low-noise converter 53. The switching matrix 52 may be embodied to switch the radio-frequency antenna unit 19 from receive mode into transmit mode and vice versa. The receive path further includes a receive-coil channel selector 57 to which any local coils 56 may be connected. The receive-coil channel selector 57 is used as a switching matrix that distributes the receive channels to the receivers provided.

In addition, the receive path includes an analog receiving unit 58 in which the receive signals are digitized and a digital receiving unit 59 in which the data rate of the digitized signals may be reduced. The digitized and reduced receive signals are further processed in a measurement acquisition and reconstruction system 60. The measurement acquisition and reconstruction system may include a computer with dedicated control hardware of the magnetic resonance apparatus 10. A control unit 61 controls previously named components of the receive paths.

A time generator 24 generates a time signal that is provided to different assemblies of the receive paths (e.g., the analog receiving unit 59 and the digital receiving unit 59). Between two boot-ups of the magnetic resonance apparatus 10, a change in the phases of the time signal at the different components (e.g., assemblies) of the receive paths may result in a change in the signal phase between the two receive channels 0° and 90°.

The components that generate and/or process the time signal lie in a section B-C of the entire receive path A-C. Hence, the receive path may be divided into a first section A-B and a second section B-C, where a constant component of the signal phase may be determined using the first section A-B and the variable component of the signal phase using the second section B-C. This will be explained below with reference to FIG. 3.

In act 100', during a first tune-up of a magnetic resonance apparatus 10, in addition to an entire receive path A-C, which represents a combination of a constant component and a variable component of the signal phase, the section B-C, which represents the variable component of the signal phase, is also measured with respect to amplitudes and phase properties. In one embodiment, a phantom 50 is that emits magnetic resonance signals after excitation is used. For the entire receive path A-C, the phase $\Phi_{AC,tuneup}$ is obtained, and for the section B-C, the phase $\Phi_{BC,tuneup}$ is obtained. These data items are filed in a persistent memory 27 as part of the calibration. The signal phase $\Phi_{AC,recon}=\Phi_{AC,tuneup}$ may be used for the reconstruction of magnetic-resonance images.

Following a start-up (e.g., boot-up) of the magnetic resonance apparatus 10 in act 110', in act 120', the phase angle for the section B-C is determined by a short measurement so that $\Phi_{BC,reboot}$ is obtained. Herein, it is possible to dispense with the use of a phantom 50.

In one embodiment, the variation in the signal phase between two boot-ups may be determined since only the section B-C is affected thereby, and this may be recalibrated without a phantom 50. On calibration of the signal phase, the correction phase $\Phi_{BC,cor}=\Phi_{BC,reboot}-\Phi_{BC,tuneup}$ is obtained with which the signal phase may be determined again for the reconstruction $\Phi_{AC,recon}=\Phi_{AC,tuneup}+\Phi_{BC,cor}$.

In other words, the signal phase for the reconstruction may be written as $\Phi_{AC,recon}=\Phi_{AC,tuneup}-\Phi_{BC,tuneup}+\Phi_{BC,reboot}=\Phi_{AB,tuneup}+\Phi_{BC,reboot}$ (e.g., the signal phase $\Phi_{AC,recon}$ for the entire receive path A-C includes the constant component $\Phi_{AB,tuneup}$ for the section A-B and the variable component $\Phi_{BC,reboot}$ for the section B-C).

A new value is thus obtained for the phase weighting of any image combinations to compensate for the influence of effects that are not constant between multiple start-ups (e.g., caused by the clock generator 24).

The example shown in FIG. 4 only includes two signal channels. However, the principle may easily be extended to more than two signal channels. For more than two signal channels, a test signal (e.g., a TTX signal) that is generated by the test signal generator 54 is sent via the body-coil channel selector 55 (e.g., the switching matrix 52) or another signal distributor simultaneously and/or in series to a plurality of receive channels that may then be calibrated with respect to one another. In other words, sending the TTX signal enables the provision of a reference path for calibration.

Figure 5:
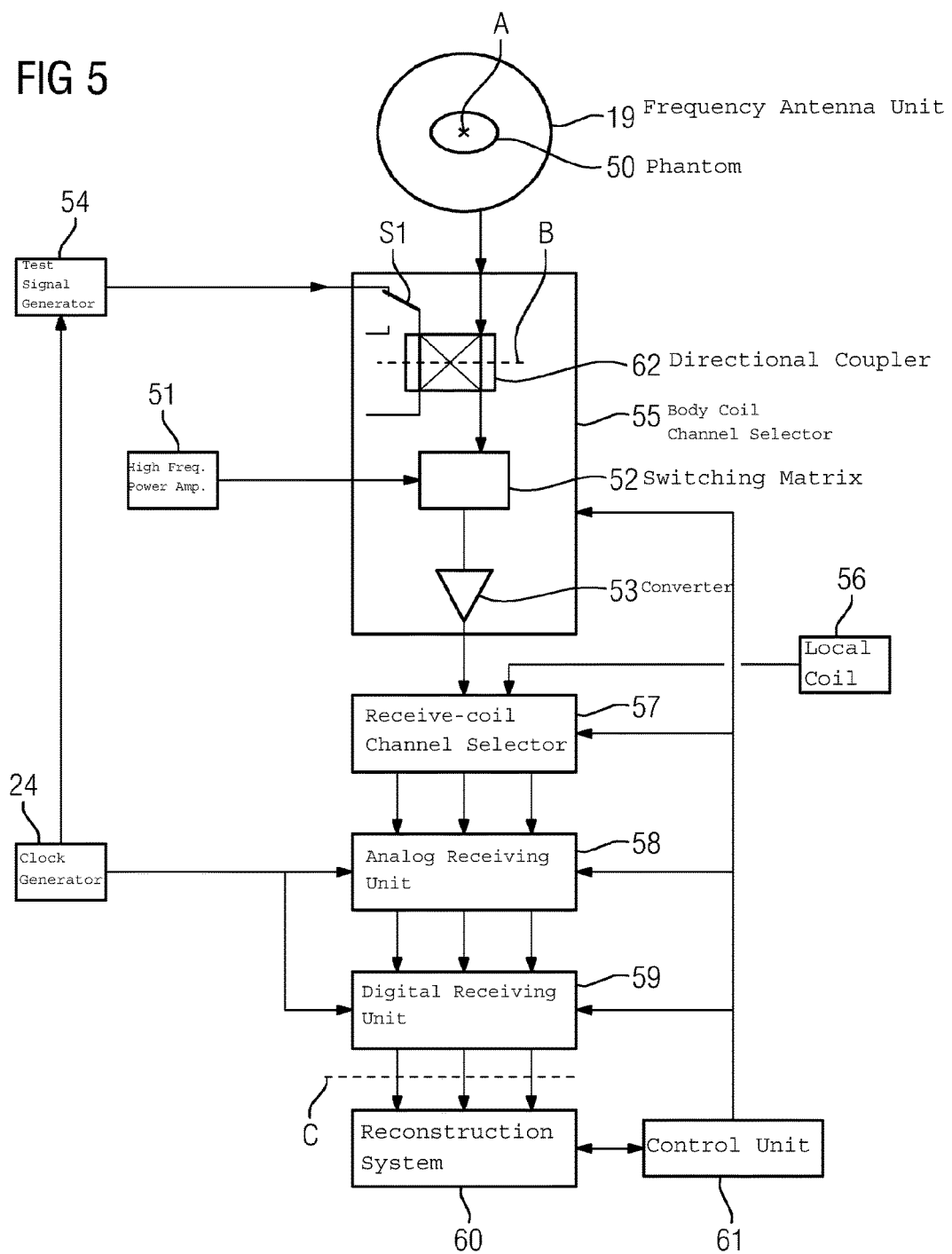
FIG. 5 shows a block diagram of a further variant of a receive path.

FIG. 5 depicts a further variant of a block diagram of a receive path. The body-coil channel selector 55 includes a directional coupler 62 that is connected via a switch S1 to the test signal generator 54. The directional coupler 62 is conventionally used to measure forward and reflected waves of the high-frequency power amplifier 51, which are, for example, caused by reflection on the radio-frequency antenna unit 19.

A test signal of the test signal generator 54 may be supplied via the directional coupler 62 or also via the switch S1. For example, the switch S1 may be arranged where at present a forward signal is output and to supply the test signal via the switch from where the test signal is transmitted to the digital receiving unit 59 in the section B-C.

In simple terms, FIG. 5 only depicts one directional coupler 62. In one embodiment, the body-coil channel selector 55 may include two or more directional couplers 62 that are, for example, switched in series between the radio-frequency antenna unit 19 and the switching matrix 52.

In one embodiment, a boot-up or a power outage on all components of the receive chain that generate and/or process a time signal is identified, and proceeding therefrom, the receive chain is automatically recalibrated. The calibration process may be carried out in approximately 10 to 1000 ms.

Reference is made once again to the fact that the methods described above in detail and the magnetic resonance apparatus depicted are exemplary embodiments only, which may be modified in wide ranges by the person skilled in the art without departing from the scope of the invention. The use of the indefinite article "a" or "an" does not preclude the possibility that the features in question may also be present on a multiple basis. Similarly, the term "unit" does not preclude the possibility of the components in question consisting of a plurality of interacting part-components, which may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for calibrating at least one operating parameter of a magnetic resonance apparatus, wherein the at least one operating parameter comprises a constant component and a variable component, the method comprising:
    starting up at least one part of the magnetic resonance apparatus, wherein starting up comprises providing a power supply to the at least one part of the magnetic resonance apparatus, and wherein the starting up leads to a change in the at least one operating parameter;
    determining, by a processor, the variable component of the at least one operating parameter and providing the constant component of the at least one operating parameter; and
    calibrating, by the processor, the at least one operating parameter using the constant component and the variable component.

2. The method of claim 1, wherein starting up the at least one part of the magnetic resonance apparatus further comprises a boot-up of the at least one part of the magnetic resonance apparatus, a switching-on of the at least one part of the magnetic resonance apparatus, a restoration of the power supply to the at least one part of the magnetic resonance apparatus, or any combination thereof.

3. The method of claim 1, further comprising identifying the starting up of the at least one part of the magnetic resonance apparatus,
    wherein the determining and the calibrating are carried out when the starting up is identified.

4. The method of claim 1, wherein the at least one operating parameter comprises a signal phase between at least two signal channels of the magnetic resonance apparatus.

5. The method of claim 4, wherein the at least two signal channels comprise transmit channels, receive channels, or the transmit channels and the receive channels.

6. The method of claim 4, wherein the at least two signal channels each comprise a signal path with a first section and a second section, and
    wherein the constant component of the at least one operating parameter is determined by the first section, and the variable component of the at least one operating parameter is determined by the second section.

7. The method of claim 6, wherein the second section comprises at least one component that generates, processes, or generates and processes a clock signal.

8. The method of claim 6, wherein the first section comprises a transmission link of an excited atomic core to a receive antenna, a transmission link from the receive antenna to a body-coil channel selector, a transmission link from a transmit antenna to an atomic nucleus to be excited, a transmission link from a body-coil channel selector to the transmit antenna, or any combination thereof.

9. The method of claim 6, wherein the second section comprises a transmission link from a body-coil channel selector to a receive-coil channel selector, a transmission link from the receive-coil channel selector to an analog receiving unit, a transmission link from the analog receiving unit to a digital receiving unit, or any combination thereof.

10. The method of claim 4, wherein determining the variable component of the at least one operating parameter comprises sending a test signal simultaneously, in series, or simultaneously and in series to the at least two transmit channels.

11. A magnetic resonance apparatus comprising:
    a processor for calibrating at least one operating parameter of the magnetic resonance apparatus, wherein the at least one operating parameter comprises a constant component and a variable component, the processor being configured to:
        start up at least one part of the magnetic resonance apparatus, wherein starting up comprises providing a power supply to the at least one part of the magnetic resonance apparatus, and wherein the starting up leads to a change in the at least one operating parameter;
        determine the variable component of the at least one operating parameter and providing the constant component of the at least one operating parameter; and
        calibrate the at least one operating parameter using the constant component and the variable component.

12. The magnetic resonance apparatus of claim 11, further comprising at least two signal channels.

13. The magnetic resonance apparatus of claim 11, further comprising at least one clock generator.

14. The magnetic resonance apparatus of claim 11, further comprising a measuring unit configured to determine the variable component of the at least one operating parameter, a calibrating unit configured to use the constant component and the variable component of the at least one operating parameter to calibrate the at least one operating parameter, or a combination thereof.

15. In a non-transitory computer-readable storage medium storing instructions executable by a calibrating unit of a magnetic resonance apparatus to calibrate at least one operating parameter of a magnetic resonance apparatus, wherein the at least one operating parameter comprises a constant component and a variable component, the instructions comprising:
    starting up at least one part of the magnetic resonance apparatus, wherein starting up comprises providing a power supply to the at least one part of the magnetic resonance apparatus, and wherein the starting up leads to a change in the at least one operating parameter;
    determining the variable component of the at least one operating parameter and providing the constant component of the at least one operating parameter; and calibrating the at least one operating parameter using the constant component and the variable component.

\* \* \* \* \*